United States Patent [19]

Sorensen et al.

[11] Patent Number: 4,706,684
[45] Date of Patent: Nov. 17, 1987

[54] AMBULATORY BLOOD PRESSURE APPARATUS

[75] Inventors: Jay R. Sorensen; Joseph D. LaPerna, both of Beaverton, Oreg.

[73] Assignee: SpaceLabs, Inc., Bothell, Wash.

[21] Appl. No.: 880,250

[22] Filed: Jun. 30, 1986

[51] Int. Cl.$^4$ .............................................. A61B 5/02
[52] U.S. Cl. ..................................... 128/677; 128/686
[58] Field of Search ..................... 128/672, 677–686; 137/602

[56] References Cited

U.S. PATENT DOCUMENTS

| | | | |
|---|---|---|---|
| 2,518,569 | 8/1950 | Pierson | 137/602 |
| 4,378,807 | 4/1983 | Peterson et al. | 128/677 |
| 4,417,587 | 11/1983 | Ichinomiya et al. | 128/682 |
| 4,501,280 | 2/1985 | Hood, Jr. | 128/686 X |

Primary Examiner—William E. Kamm
Assistant Examiner—Angela D. Sykes
Attorney, Agent, or Firm—Seed and Berry

[57] ABSTRACT

An ambulatory blood pressure monitor comprises a cuff coupled by a single fluid passageway to a manifold which in turn is coupled to a pump, valve and pressure transducer. The manifold comprises a larger main chamber in fluid communication with a smaller secondary chamber through a small channel in a wall separating the chambers. The pump, cuff and valve are in fluid communication with one another directly through the main chamber while the pressure transducer is coupled to the cuff through the secondary chamber.

10 Claims, 7 Drawing Figures

AMBULATORY BLOOD PRESSURE APPARATUS

BACKGROUND OF THE INVENTION

The present invention relates to an automatic blood pressure monitoring apparatus, more particularly, to ambulatory blood pressure monitoring.

A number of portable monitoring devices are used in medical monitoring. One well known device is the so-called Holter monitor which is an EKG monitor which typically uses a magnetic tape recording to record EKG signals from a patient over extended periods of time. Another is a portable monitor for obtaining blood pressure readings over extended periods of time. An example of such a monitor is the Model 5200 ambulatory blood pressure monitor sold by SpaceLabs, Inc. of Redmond, WA.

The Model 5200 comprises a blood pressure cuff, an air pump for activating the blood pressure cuff, a pressure transducer for generating electrical signals representative of the pressure in said cuff, circuitry and means for processing the electrical signals and a removable RAM package for storing the blood pressure data resulting from processing the electrical signals.

In the prior art, one air hose is provided from the air pump to the cuff bladder to pump up the cuff and to bleed the cuff while a second air hose is provided between the bladder and the pressure transducer for sensing the cuff pressure by the pressure transducer.

Unwanted surges of pressure as the bladder is pumped up or as stepped bleeding occurs are coupled into the pressure transducer which causes unwanted noise or spurious electrical signals to be generated by the transducer. Also, in the particular case of an ambulatory monitor which is often worn by the patient all day and night, the smaller and lighter the monitor, the better. In particular it is desirable to reduce the number of air hoses which must be coupled to the cuff from the usual two hoses to one hose.

SUMMARY OF THE INVENTION

An ambulatory blood pressure (ABP) monitor is provided having a cuff coupled through a single fluid passageway to a manifold which in turn is coupled to a pump, a valve and pressure transducer. The manifold includes a larger main chamber in fluid communication through a small channel to a small secondary chamber. The cuff, pump and valve are coupled together in fluid communication directly through the main chamber while the pressure transducer is coupled to the main chamber through the secondary chamber. The volume of the main chamber is about an order of magnitude greater than the secondary chamber and about three orders of magnitude greater than the small channel.

DETAILED DESCRIPTION OF THE DRAWINGS

Figure 1:
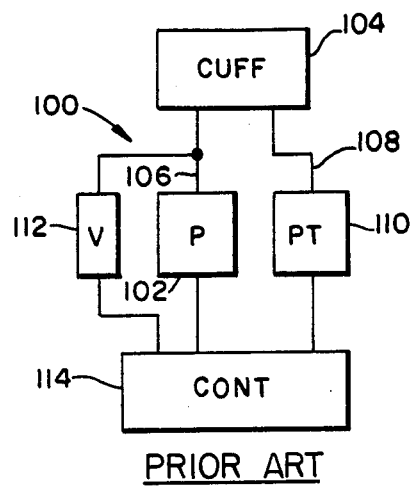
FIG. 1 is a block diagram of a prior art ambulatory blood pressure monitor coupled to a cuff.

Referring now to FIG. 1, a prior art block diagram of an ambulatory blood pressure (ABP) monitor designated generally 100 is shown coupled to cuff 104. It comprises an air pump 102 coupled to an air bladder (not shown) within cuff 104 by an air hose 106. The bladder is also coupled via separate air hose 108 to the ABP pressure transducer 110. The ABP valve 112 is coupled to the pump/cuff connector 106 to allow air to bleed from the bladder. Usually the valve, pump and pressure transducer are all coupled to an ABP controller 114 such as a microprocessor controller for controlling the pumping and bleeding of the cuff and the processing of the transducer output signals.

In response to the controller 114, in one mode of operation, pump 102 pumps air into the cuff 104 increasing the applied air pressure therein. The applied pressure in the cuff is then bled down in a series of steps by activating the valve 112 in response to commands from the controller 114. At each step the total pressure in the cuff is sensed by the transducer 110. Because the transducer is coupled by its own separate air tube 108 the perturbations to the pressure in the bladder caused by the pumping or bleeding operations is coupled to the pressure transducer causing spurious or noise like output signals. In addition, as mentioned before, two air hoses coupled to the cuff are required instead of one making it more cumbersome for the user.

Figure 2:
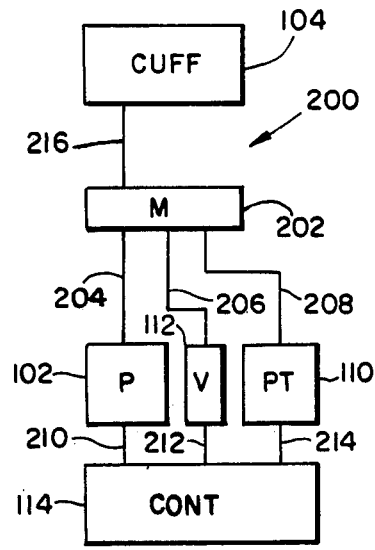
FIG. 2 is a block diagram of a preferred embodiment ambulatory blood presure monitor including a manifold of the present invention coupled to a cuff.

A block diagram of the present invention ABP monitor designated generally 200 is shown in FIG. 2 coupled to the cuff 104. The ABP monitor 200 comprises the pump 102, valve 112 and pressure transducer 110 all coupled to a manifold 202 via air tubes 204, 206 and 208, respectively and to the controller 114 via air tubes 210, 212 and 214, respectively. Manifold 202 is also coupled to cuff 104 via a single air hose 206. In the preferred embodiment the air hose is made from a polymer plastic such as polyvinylchloride with a 0.125 inch internal diameter, a 0.250 inch outer diameter and a dorometer rating of 70. The pump, valve and pressure transducer are all coupled to cuff 104 via manifold 202 and are controlled by controller 114 to operate in a manner as described for the prior art ABP of FIG. 1.

Referring now to FIGS. 3 through 6, the manifold 202 of the present invention is shown in more detail. It comprises a main rectangularly shaped plastic housing designated generally 302 having four side walls even numbers 304 through 310 and a top surface 312 defining an interior region designated generally 314. The manifold further comprises four generally cylindrically shaped members even numbers 320 through 326 integrally formed with an extending from the top surface 312. The members 320 through 326 are hollow and open to the interior region 314 at apertures even numbers 330 through 336, respectively, in surface 312 and open at their distal ends even numbers 340 through 346, respectively, such that the interior region 314 of the manifold is in communication through the members 320 through 326 with ambient atmosphere.

The manifold 202 further comprises a rectangular flat insert 348 which is adapted for closing off the bottom of the main body 302 to further enclose interior region 14 and form the bottom surface of the manifold. The insert rests against the interior ledge 350 and is attached by gluing, etc.

Interior region 314 is divided into a main chamber 360 and a smaller secondary chamber 362 by the interior walls 364 and 366. The interior of the main chamber 360 communicates with the interior of the secondary chamber 362 through a rectangularly shaped channel 370 through the wall 364. The channel 370 acts as a means for providing restricted fluid communication between the main chamber and secondary chamber.

The volume of the main chamber in the preferred embodiment is 6 to 7 times the volume of the smaller chamber. The dimensions of the interior region in the preferred embodiment are 0.720 inches by 0.195 inches with a depth of 0.060 inches. The ledge 350 has a width of about 0.010 inches while the insert is approximately 0.740 inches by 0.215 inches with a thickness of 0.04 inches. The hole or channel 370 is 0.020 inches high and 0.010 inches wide.

The cylindrical interior 380 and 382 of members 320 and 322, respectively, each have a diameter of 0.0825 inches and a height of 0.290 inches and their bottoms open into main chamber 360 through apertures 330 and 332, providing fluid communication with the main chamber separate from the restricted fluid communication provided by chamber 370, while the cylindrical interiors 384 and 386 of members 324 and 326 respectively have a smaller diameter of 0.0375 inches and a height of 0.240 inches. Member 324 also opens up into main chamber 360 through aperture 334 (also providing fluid communication thereto separate from channel 370) but member 326 opens up into the secondary chamber 362 through aperture 336 (providing fluid communication to the secondary chamber separate from the channel 370).

Figure 7:
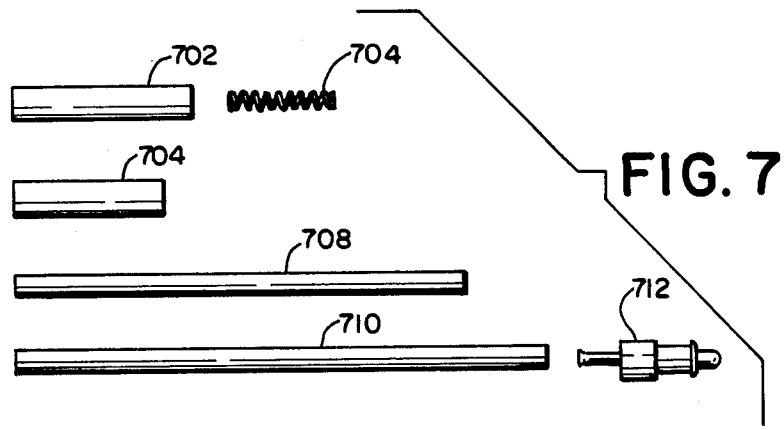
FIG. 7 shows tubing sections for coupling to the manifold for easier access thereto.
Figure 3:
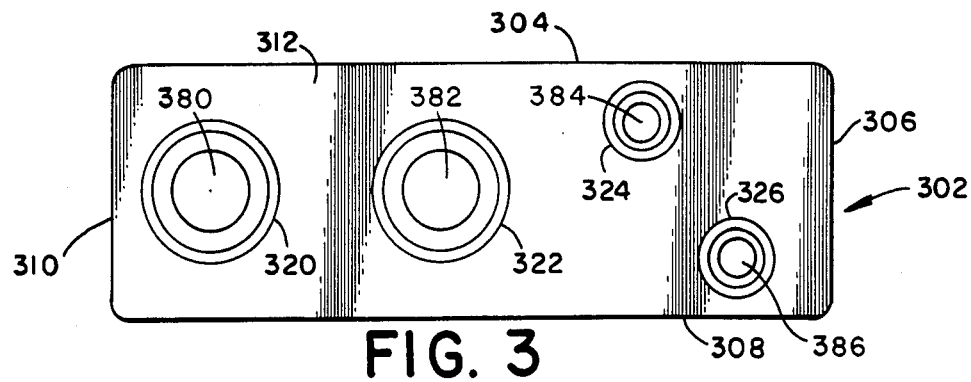
FIG. 3 is a top planar view of the manifold of the present invention.
Figure 4:
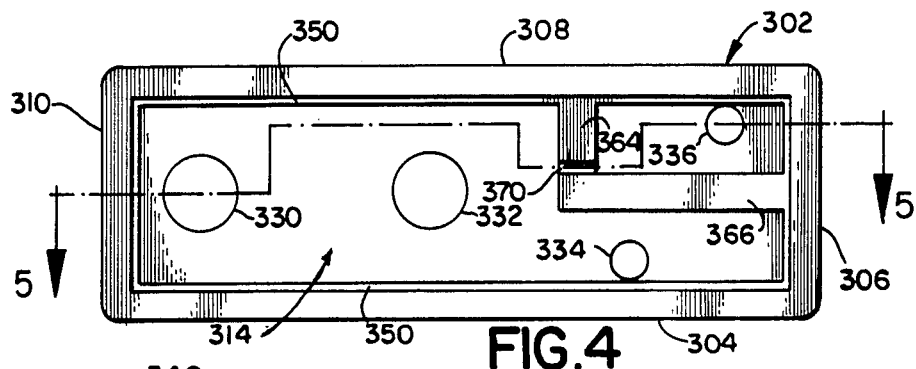
FIG. 4 is a bottom planar view of the manifold of the present invention with the bottom insert removed.
Figure 5:
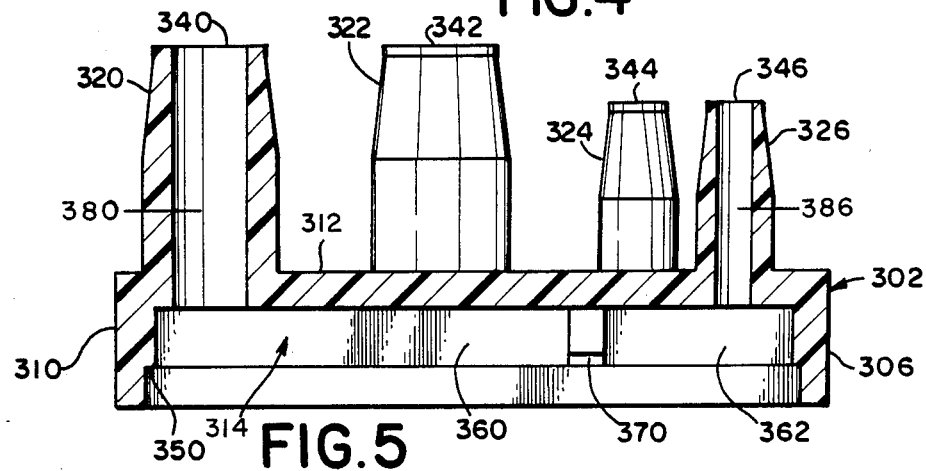
FIG. 5 is an elevational cross sectional view of the present invention manifold taken along the lines and arrows 5—5 in FIG. 4.
Figure 6:
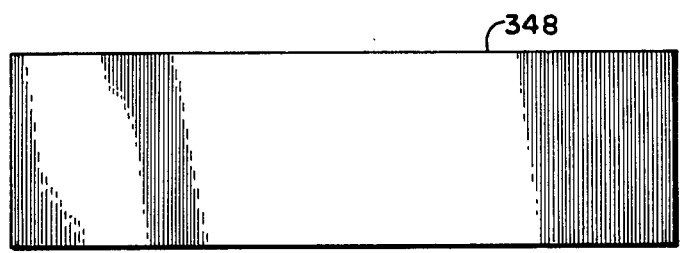
FIG. 6 is a planar view of the bottom insert for the manifold of FIGS. 3 through 5.

The outside wall of the distal end of each of the members 320 through 326 is tapered to provide easy insertion into an open end of flexible tubing adapted for coupling the manifold 202 to various other parts of the ABP monitor as described in connection with FIG. 2. Referring to FIG. 7, a one inch long piece of tubing 702 with a 0.104 inch internal diameter is provided for coupling engagement with coupling member 320. A stiffening spring 704 may be provided for insertion into the tubing 702. A larger piece of flexible air hose as described earlier represented by line 216 with suitable fitting at either end is used to couple coupling member 320 with tubing 702 to the bladder of cuff 104.

Similarly, a 0.75 inch long piece of tubing 706 with a 0.104 inch internal diameter is provided for coupling engagement with coupling member 322. A shorter piece of flexible tubing represented by line 204 in FIG. 2 couples the manifold to the pump 102.

A three inch long 0.042 inch internal diameter tubing 708 couples the coupling member 324 to the valve 112. A 3.5 inch long, 0.042 inch internal diameter tubing 710 is provided for coupling the coupling member 326 to the pressure transducer 110. A reducer fitting 712 is used to couple the smaller diameter tubing 710 to the air hose 208 which is a 0.125 inch diameter line.

In operation the pump 102 pumps air through the interior of coupling member 322, main chamber 360, the interior of coupling member 320 to the bladder of cuff 104. Air is bled from the cuff through the interior of coupling member 320, main chamber 360 and the interior of coupling member 324 through valve 112. The pressure transducer 110 is able to sense the pressure in the cuff through the interior of coupling member 326, the secondary chamber 362, the channel 370, main chamber 360 and the interior of coupling member 320. Large perturbations to the pressure in the main chamber due to repeated pumping action by the pump or step bleeding by the valve are reduced by the small opening of the channel 370 linking the main chamber 360 with the secondary chamber 362. The channel 370 acts as a pneumatic air filter to filter out perturbations and provide smoothed air pressure input to the transducer. The manifold further makes it possible to use only a single air hose connecting the pump, valve and pressure transducer to the cuff where before two hoses were required.

What is claimed is:

1. In an ambulatory blood pressure monitor including a cuff, a pump for increasing fluid pressure in the cuff and a pressure transducer means for sensing the fluid pressure in the cuff and generating signals in response thereto, the improvement comprising:
    a manifold coupled to said cuff by a single fluid passageway, and further coupled to said pump, valve and pressure transducer, said manifold further comprising:
    a main body having an interior region comprising a main chamber and a separate secondary chamber;
    means for providing restricted fluid communication between said main chamber and said secondary chamber;
    a first means for providing fluid communication between said main chamber and said pump separate from said restricted providing means;
    a second means for providing fluid communication between said main chamber and said cuff separate from said restricted providing means; and
    a third means for providing fluid communication between said secondary chamber and said pressure transducer means separate from said restricted providing means.

2. The monitor of claim 1 wherein said first, second and third providing means comprise first, second and third coupling members, respectively, coupling the manifold to said pump, cuff and pressure transducer means, respectively, said first and second coupling members each having a hollow interior in fluid communication with said main chamber separate from said restricted providing means and said third coupling member having a hollow interior in fluid communication with said secondary chamber separate from said restricted providing means.

3. The monitor of claim 2 wherein said main chamber and secondary chamber are separated by an interior wall and said restricted providing means comprises a channel through said wall.

4. The manifold of claim 3 wherein said main chamber has a volume which is two to ten times greater than the volume of said secondary chamber and approximately three orders of magnitude greater than the volume of said channel.

5. The manifold of claim 4 wherein the volume of said main chamber is approximately an order of magnitude greater than said secondary chamber.

6. The monitor of claim 1 wherein said manifold further comprises fourth means for providing a fluid communication between said main chamber and said valve separate from said restricted providing means.

7. The monitor of claim 6 wherein said first, second, third and fourth providing means comprise first, second, third and fourth coupling members, respectively, coupling the manifold to said pump, cuff, pressure transducer means and valve, respectively, said first, second and fourth coupling members each having a hollow interior in fluid communication with said main chamber separate from said restricted providing means and said third coupling member having a hollow interior in fluid communication with said secondary chamber separate from said retricted providing means.

8. The monitor of claim 7 wherein said main chamber and secondary chamber are separated by an interior wall and said restricted providing means comprises a channel through said wall.

9. The manifold of claim 7 wherein said main chamber has a volume which is two to ten times greater than the volume of said secondary chamber and approximately three orders of magnitude greater than the volume of said channel.

10. The manifold of claim 9 wherein said main chamber has a volume which is approximately an order of magnitude greater than the volume of said secondary chamber and approximately three orders of magnitude greater than the volume of said channel.

* * * * *